US005591889A

United States Patent [19]
Jakupovic et al.

[11] Patent Number: 5,591,889
[45] Date of Patent: Jan. 7, 1997

[54] METHOD FOR THE SYNTHESIS OF TRISODIUM PHOSPHONOFORMATE HEXAHYDRATE

[75] Inventors: Edib Jakupovic, Nykvarn; Jan Stenhede, Södertälje, both of Sweden

[73] Assignee: Aktiebolaget Astra, Sodertalje, Sweden

[21] Appl. No.: 425,344

[22] Filed: Apr. 18, 1995

Related U.S. Application Data

[63] Continuation of Ser. No. 91,475, Jul. 14, 1993, abandoned, which is a continuation of Ser. No. 773,621, filed as PCT/SE91/00172, Mar. 6, 1991, abandoned.

[51] Int. Cl.$^6$ .................................................. C07F 9/22
[52] U.S. Cl. ............................................................. 562/24
[58] Field of Search ................................................ 562/24

[56] References Cited

U.S. PATENT DOCUMENTS 4,018,854  4/1977  McIntosh ........................... 260/941
4,966,991  10/1990  Gerdau ................................ 562/23

FOREIGN PATENT DOCUMENTS 253848  8/1988  Czech Rep. ............................ 562/23

*Primary Examiner*—Marianne M. Cintins
*Assistant Examiner*—Keith MacMillan
*Attorney, Agent, or Firm*—White & Case

[57] ABSTRACT

The present invention relates to a method for the synthesis of foscarnet, i.e. trisodium phosphonoformate hexahydrate, comprising the steps of adding sodium hydroxide to water, heating the aqueous sodium hydroxide solution to 50° C., adding triethyl phosphonoformate to said solution at 50° C., heating the reaction mixture to reflux for about 1 hour, cooling of the reaction mixture and filtering-off of the product.

8 Claims, No Drawings

METHOD FOR THE SYNTHESIS OF TRISODIUM PHOSPHONOFORMATE HEXAHYDRATE

This application is a continuation of application Ser. No. 08/091,475, filed Jul. 14, 1993 (abandoned), which is a continuation of application Ser. No. 07/773,621, filed as PCT/SE91/00172 Mar. 6, 1991, (abandoned).

TECHNICAL FIELD

The present invention relates to a method for the synthesis of foscarnet, i.e. trisodium phosphonoformate hexahydrate.

PRIOR ART

EP-A-241 686 discloses a process for the synthesis of alkali phosphonoformates comprising the steps of mixing trialkyl phosphonoformate and aqueous alkali hydroxide at a temperature between the freezing point of water and 40° C., optionally maintaining the reaction mixture at this temperature for a while, and then heating the reaction mixture to reflux in order to obtain complete saponification.

The product is then recovered by maintaining the reaction mixture at about 0° C. for 24 hours, the crystals are separated off and are then recrystallized. The reported yield is 80% to 86%, and the purity 99,9%.

However, it has been found that the water content, which should be 36% in the dry product in hexahydrate form, varies when following the disclosed procedure.

SUMMARY OF THE INVENTION

The object of the present invention is to provide a method for the synthesis of trisodium phosphonoformate hexahydrate.

This object is achieved according to the present invention which is characterized by the steps of adding sodium hydroxide to water, heating the aqueous sodium hydroxide solution to 50° C., adding triethyl phosphonoformate to said solution at 50° C., heating the reaction mixture to reflux temperature for about 1 hour, cooling of the reaction mixture and filtering-off of the product.

According to one embodiment of the invention, the product is dissolved in water and is then recrystallized by cooling the solution to about 20° C. giving trisodium phosphonoformate hexahydrate.

According to another embodiment of the invention, the product is dissolved in water and is then recrystallized by cooling the solution to about 5° C., resulting in the formation of trisodium phosphonoformate dodecahydrate, which is dried to give trisodium phosphonoformate hexahydrate.

DISCLOSURE OF PREFERRED EMBODIMENTS

According to the invention, in a first step sodium hydroxide in concentrated form is mixed with water and the solution is heated to about 50° C. Then triethyl phosphonoformate is added to the solution at 50° C. The temperature of the reaction mixture is raised to reflux temperature, which is about 90°–95° C., and ethanol formed is distilled off. After a suitable time at reflux temperature, which would be about 1 hour, the reaction mixture is cooled and the product is filtered off.

By cooling to a temperature of not lower than about 17° C., preferably not lower than 20° C., will result in the formation of trisodium phosphonoformate hexahydrate in wet state. The water content will thus be above 36%, which is the water content of the dry product in pure form. Cooling to a temperature of above 20° C. will lead to reduced yield. As a suitable upper limit, where adequate yield still is obtained may be mentioned 25° C. to 30° C.

Cooling to aboout 5° C. or below will result in the formation of trisodium phosphonoformate dodecahydrate. Upon drying of this compound under suitable conditions the product in dodecahydrate form will successively transform into the hexahydrate form. If the drying process is driven to far the product will successively transform into nonhydrated trisodium phosphonoformate.

Preferably the product obtained in the process according to the invention is recrystallized by dissolving it in water, heating the solution in order to obtain a clear solution, which then is cooled down to about 20° C. in order to obtain the product in hexahydrate form or down to about 5° C. in order to obtain the product in dodecahydrate form for subsequent drying.

The invention will now be illustrated by two working examples.

EXAMPLE 1

423 g (4.77 mol) of sodium hydroxide liquid conc. is added to 400 ml of water. The solution is heated to about 50° C. and 167 g (0.795 mol) of triethyl phosphonoformate is added at this temperature. The reaction mixture is then heated to about 90° C. and ethanol formed is distilled off. After about 1 hour at 90°–95° C. the reaction mixture is cooled to about 20° C. and the product is filtered off. The yield of trisodium phosphonoformate hexahydrate wet is 248 g.

The wet substance is recrystallized in 570 ml of water by heating to 90° C. in order to obtain a clear solution and then cooling to about 20° C. After filtration and washing with 50 ml of water at 18°–22° C. 187 g (74% of theoretical yield) of trisodium phosphonoformate hexahydrate is obtained. This substance contains about 2% free water, which can be eliminated by drying.

EXAMPLE 2

93.5 g trisodium phosphonoformate hexahydrate is dissolved in 335 ml of water by heating to 90° C. to obtain a clear solution and is then cooled to about 5° C. After filtration 119 g of trisodium phosphonoformate dodecahydrate is obtained. Drying of this substance under suitable conditions will result in the formation of trisodium phosphonoformate hexahydrate.

We claim:

1. A method for the preparation of trisodium phosphonoformate hexahydrate, comprising the steps of adding sodium hydroxide to water; heating the aqueous sodium hydroxide solution to 50° C.; adding triethyl phosphonoformate to said solution at 50° C. so as to produce a reaction mixture containing trisodium phosphonoformate and ethanol; heating the reaction mixture to reflux temperature for about 1 hour for removing the ethanol; cooling the reaction mixture to a temperature between about 17° C. and about 30° C.; and filtering off the product, trisodium phosphonoformate hexahydrate.

2. A method for the preparation of trisodium phosphonoformate hexahydrate, comprising the steps of adding sodium hydroxide to water; heating the aqueous sodium hydroxide solution to 50° C.; adding triethyl phosphonoformate to said solution at 50° C. so as to produce a reaction mixture; heating the reaction mixture to a temperature of 90° C.–95° C. for about 1 hour; cooling the reaction mixture of 20° C.–30° C.; and filtering off the crystalline product.

3. A method for the preparation of trisodium phosphonoformate hexahydrate, comprising the steps of adding sodium hydroxide to water, heating the aqueous sodium hydroxide solution to 50° C., adding triethyl phosphonoformate to said solution at 50° C. so as to produce a reaction mixture containing trisodium phosphonoformate acid and ethanol, heating the reaction mixture to a temperature of 90° C.–95° C. for about 1 hour so as to remove the ethanol, cooling the reaction mixture to about 20° C. and filtering off the crystalline trisodium phosphonoformate product.

4. The method according to claim 1, 2, or 3 additionally comprising the subsequent steps of dissolving the product in water and then recrystallizing by cooling the solution to a temperature ranging from about 20° C. to about 30° C. so as to produce trisodium phosphonoformate hexahydrate.

5. The method according to any one of claims 1, 2 or 3 additionally comprising the subsequent steps of dissolving the product in water and then recrystallizing by cooling the solution to 20° C. giving trisodium phosphonoformate hexahydrate.

6. The method according to claim 1 wherein the reflux temperature is about 90° C. to about 95° C.

7. A method for the preparation of crystalline trisodium phosphonoformate hexahydrate comprising the steps of (a) adding a suitable amount of sodium hydroxide to water so as to make an approximately 5.8M aqueous sodium hydroxide solution;

(b) heating the aqueous sodium hydroxide solution to 50° C.;

(c) maintaining the aqueous sodium hydroxide solution at 50° C. while admixing triethyl phosphonoformate at a molar ratio to sodium hydroxide of about 1:6 so as to produce a reaction mixture containing trisodium phosphonoformate and ethanol;

(d) evaporating the ethanol by heating the admixture to a temperature range of about 90° C. to about 95° C. for a time sufficient to evaporate the ethanol;

(e) cooling the admixture to a temperature of not less than about 17° C. and no more than about 30° C. so as to precipitate the crystalline trisodium phosphonoformate hexahydrate product; and (f) filtering off the crystalline product.

8. The method according to claim 7, wherein the admixture is cooled to a temperature range of about 20° C. to about 25° C.

* * * * *